United States Patent
Bath et al.

(10) Patent No.: US 6,455,558 B1
(45) Date of Patent: Sep. 24, 2002

(54) BIOCIDE COMPOSITION AND USE

(75) Inventors: Colin Bath, Manchester (GB); John David Payne, Manchester (GB); Paula Louise McGeechan, Manchester (GB)

(73) Assignee: Avecia Limited, Blackley (GB)

( * ) Notice: Subject to any disclaimer, the term of this patent is extended or adjusted under 35 U.S.C. 154(b) by 0 days.

(21) Appl. No.: 09/857,126

(22) PCT Filed: Oct. 18, 1999

(86) PCT No.: PCT/GB99/03422

§ 371 (c)(1),
(2), (4) Date: Aug. 23, 2001

(87) PCT Pub. No.: WO00/33656

PCT Pub. Date: Jun. 15, 2000

(30) Foreign Application Priority Data

Dec. 9, 1998 (GB) ................................. 9826963

(51) Int. Cl.⁷ ................. A01N 43/80; A01N 43/62; A01N 43/58; A01N 43/26; A61K 31/425
(52) U.S. Cl. ...................................... 514/372
(58) Field of Search ................. 514/372, 212, 514/218, 247, 277, 439

(56) References Cited

FOREIGN PATENT DOCUMENTS

| | | | |
|---|---|---|---|
| GB | 2 230 190 | | 10/1990 |
| JP | 6227912 | * | 8/1994 |
| WO | 2230190 | * | 10/1990 |
| WO | WO 92/01380 | | 2/1992 |
| WO | 9201380 | * | 2/1992 |
| WO | WO 96/22023 | | 7/1996 |

OTHER PUBLICATIONS

Database WPI, Derwent Publications Ltd., London, GB; AN 1994–299634 XP002130691 Sekisui Chem Ind Co Ltd: "Antimicrobial sealing compsns. to present surface contamination–comprising denaturated silicone, zinc salt of bis (2–pyridylthiol–1–oxide) and antifungal cpd(sO.e.g. benzimidazole or isothiazoline cpds." abstract & JP 06 227912 A.

* cited by examiner

Primary Examiner—Alton Pryor
(74) Attorney, Agent, or Firm—Pillsbury Winthrop LLP

(57) ABSTRACT

A method for the preservation of a plastics material against the growth of deteriogens which comprises treating the plastics material with a composition comprising a) an isothiazolin-3-one such as N-n-octyl- or 4,5-dichloro-N-n-octyl-isothiazolin-3-one and b) the metal complex of a thiohydroxamic acid such as 2:1 zinc complex of 3-hydroxy-4-methylthiazol-2(3H)-thione or the 2:1 zinc complex of 1-hydroxypyridine-2-thione.

22 Claims, No Drawings

BIOCIDE COMPOSITION AND USE

This application is the National Phase of International Application PCT/GB99/03422 filed Oct. 18, 1999 which designated the U.S. and that International Application was published under PCT Article 21(2) in English.

The present invention relates to a biocidal composition comprising a isothiazolinone such as an N-alkyl-isothiazolin-3-one and a metal complex of a cyclic thiohydroxamic acid and its use to inhibit the growth of microorganisms in a medium which is susceptible to microbiological degradation and especially to inhibit the growth of deteriogens of plastics materials in soil burial conditions.

WO 96/22023 discloses the use of N-($C_{3-5}$-alkyl)-1,2-benzisothiazolin-3-one as a biocide and especially a fungicide for plastics materials. It has now been found that the antimicrobial activity of these and other isothiazolinones is significantly improved by incorporating a metal complex of a cyclic thiohydroxamic acid.

According to the invention there is provided a method for the preservation of a plastics material which comprises treating the plastics material with a composition comprising (a) an isothiazolinone of formula (1) and (b) a metal complex of a cyclic thiohydroxamic acid.

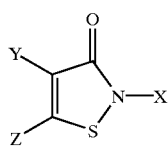

(1)

wherein:

X is $C_1$–$C_8$-alkyl, $C_{3-5}$-cycloalkyl or aralkyl; and

Y and Z are independently selected from hydrogen, halogen or $C_{1-4}$-alkyl.

Preferably, the halogen is iodine, bromine and especially chlorine.

When X is alkyl it may be linear or branched and is preferably linear.

When X is cycloalkyl, it is preferably cyclopropyl or cyclopentyl.

When X is aralkyl, it preferably contains two or more carbon atoms in the alkylene group attaching the aryl group to the isothiazolinone ring. Preferably the aralkyl group is 2-phenylethyl. Other examples of aralkyl are benzyl and 2-naphthylethyl.

It is particularly preferred that when X is n-octyl Y and Z are either both chlorine or both hydrogen. The preparation of isothiazolinones of this type is disclosed in U.S. Pat. No. 4,105,431.

The cyclic thiohydroxamic acid preferably contains a 5- or 6- membered ring which is optionally substituted. It is preferably a metal complex of a compound of formula 2

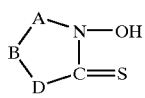

(2)

wherein

A is a group —$C(R^2)^2$—, —$C(R^2)$=or —$CR^2$=$CR^2$—;

B is a group —$C(R^2)^2$—, —$C(R^2)$=or —$C(NR^2)$—;

D is a group —$C(R^2)^2$—, —$C(R^2)$=, -$NR^2$— or sulphur;

$R^2$ is hydrogen, optionally substituted $C_{1-6}$-hydrocarbyl or two groups $R^2$ together with the carbon atom to which they are attached form a $C_{3-6}$-hydrocarbon ring or two groups $R^2$ together with the two carbon atoms to which they are attached form a fused ring.

When $R^2$ is hydrocarbyl it is preferably alkyl or phenyl and the alkyl group may be branched or preferably linear. It is particularly preferred that $R^2$ is hydrogen or $C_{1-4}$-alkyl, for example methyl.

When $R^2$ is substituted, the substituent may be any group or atom which does not significantly adversely affect the microbiological properties of the cyclic thiohydroxamic ring system. Preferred substituents are hydroxy, halogen and nitrile. It is particularly preferred that $R^2$ is unsubstituted.

When two moieties $R^2$ together with the carbon atom to which they are attached form a ring, the ring is preferably cyclohexyl.

When two moieties $R^2$ together with the carbon atoms to which they are attached form a fused ring, the ring is preferably a fused phenyl ring.

When D is sulphur, the compound of formula 2 is preferably a thiazol-2(3H)-thione wherein both A and B are either the group —$C(R^2)^2$— or especially the group —$C(R^2)$=.

When D is the group —$NR^2$—, the compound of formula 2 is preferably an imidazolidine-2-thione. When D is the group —$NR^2$—, it is also preferred that A is the group —$C(R^2)^2$— or —$C(R^2)$=and B is the group —$C(NR^2)$—.

When D is a group —$C(R^2)^2$— or a group —$C(R^2)$=, it is preferred that both A and B are also the groups —$C(R^2)^2$— or —$C(R^2)$=. In this case, the compound of formula 2 is preferably a pyrrolinethione, pyrrolidinethione or an isoindolinethione.

When A is the group —$CR^2$=$CR^2$—, it is preferably the group —CH=CH— and both B and D are the group —$C(R^2)$=when the compound of formula 2 is a pyridine-2-thione.

Examples of the compound of formula 2 are:

3-hydroxy-4-methylthiazol-2(3H)-thione, 3-hydroxy-4-phenylthiazol-2(3H)-thione, 3-hydroxy-4,5,6,7-tetrahydrobenzothiazol-2(3H)-thione, 5,5-dimethyl-1-hydroxy-4-imino-3-phenylimidazolidine-2-thione, 1-hydroxy-4-imino-3-phenyl-2-thiono-1,3-diazaspiro[4,5]-decane, 1-hydroxy-5-methyl-4-phenylimidazoline-2-thione, 4,5-dimethyl-3-hydroxythiazol-2(3H)-thione, 4-ethyl-3-hydroxy-5-methylthiazol-2(3H)-thione, 4-(4-chlorophenyl)-3-hydroxythiazol-2(3H)-thione, 3-hydroxy-5-methyl-4-phenylthiazol-2(3H)-thione, 1-hydroxypyrrolidin-2-thione, 5,5-dimethyl-1-hydroxypyrrolidin-2-thione, 2-hydroxy-2,3-dihyro-1 H-isoindol-1-thione, and 5 1-hydroxypyridine-2-thione.

The metal which forms the complex of the compound of formula 2 is preferably a metal from Groups IIIA to VA or IB to VIIB or a transition metal of the Periodic Table according to Mendeleef as set out on the inside rear cover of "Handbook of Chemistry and Physics" 49th edition (1968–9) published by The Chemical Rubber Co., Cleveland, Ohio, USA. Preferably, the metal is a metal of Group IIB and is especially zinc.

Particularly useful effects have been obtained when the isothiazolinone is either N-n-octyl-isothiazolin-3-one or 4,5-dichloro-N-n-octyl-isothiazolin-3-one and the metal complex of the compound of formula 2 is the 2:1 zinc complex of 3-hydroxy-4-methylthiazol-2(3H)-thione or the 2:1 zinc complex of 1-hydroxypyridine-2-thione. The preparation of the isothiazolinones is described in U.S. Pat No. 4,105,431 and the preparation of the cyclic thiohydroxamic acids is described in EP 249,328 and U.S. Pat. No. 5,120,856. The preparation of metal complexes of 1-hydroxypyridine-2-thione is specifically disclosed in U.S. Pat. No. 2,686,786, U.S. Pat. No. 2,758,116 and U.S. Pat. No. 2,809,971.

The relative proportions of component (a) and component (b) in the composition can vary between wide limits but is preferably from 100:1 to 1:100, more preferably from 10:1 to 1:10 and especially from 3:1 to 1:3, for example about 1:1.

The composition of the present invention has antimicrobial properties and has been found particularly effective against deteriogens for plastics materials, especially in soil burial applications.

The composition according to the invention is useful to inhibit the growth of micro-organisms in a medium which is susceptible to microbiological degradation. Component (a) and component (b) of the composition may be added to the medium either sequentially or preferably simultaneously. Where appropriate, the composition may be added directly to the medium, especially where the medium is a solid such as a plastics material. In other uses, it is more convenient to treat the medium with a composition comprising component (a), component (b) and a carrier.

As noted hereinbefore, the composition according to the invention has been found particularly useful as a biocide for inhibiting the growth of deteriogens for plastics materials, especially organic polymeric material containing a plasticiser or stabiliser.

Examples of plastics materials are polyurethanes, polyvinylhalides such as polyvinylchloride (PVC), polyalkylenes such as polypropylene, polyalkylene vinyl acetate such as polyethylene vinyl acetate, polyester such as polyethyleneterephthalate, polyamide and polyacrylonitrile. The composition has been found especially effective for inhibiting the growth of micro-organisms in or on plasticised PVC. Other suitable plastics materials are caulks and sealants, especially silicone sealants.

The amount of the composition according to the invention which is present in the plastics material may vary over wide limits from a minimum amount which just inhibits microbiological growth up to many times this amount. Thus, where the plastics material containing the composition is to be used as a master-batch for mixing with untreated plastics material the amount of the composition may be two or three magnitudes greater than that required to inhibit microbiological growth. Preferably, the amount of the composition in the plastics material which is required to inhibit microbial degradation is not less than 10, more preferably not less than 100, even more preferably not less than 500 and especially not less than 1000 ppm relative to the amount of the plastics material. It is also preferred that the amount of the composition which is required to inhibit microbial degradation is not greater than 5000 ppm, more preferably not greater than 4000 ppm and especially not greater than 3000 ppm relative to the amount of the plastics material.

The composition according to the invention may be applied to the plastics material after fabrication to form the finished article but is preferably applied to the plastics material prior to fabrication.

In one preferred method, component (a) and component (b) are applied sequentially or preferably simultaneously to the dry plastics material which may be any solid form such as powder, flake, chip or pellet to form a master-batch. Thus, according to a further aspect of the invention there is provided a master-batch which is a composition comprising a plastics material together with component (a) and component (b).

Where the plastics material is fabricated with a plasticiser or stabiliser, the composition comprising component (a) and component (b) may be conveniently added with a carrier which is a stabiliser and/or plasticiser for a plastics material.

The plasticiser or stabiliser may be any of those commonly used in the plastics material fabrication industry and is preferably a liquid. Examples of suitable plasticiser/stabiliser are esters of aromatic and aliphatic mono- and di-carboxylic acids and linear or branched alcohols especially $C_{8-10}$-alcohols; epoxidised fatty acid esters and epoxidised vegetable oils. Specific examples of plasticisers are di-hexyl-, di-octyl-, di-nonyl, di-isodecyl-, and di-(2-ethylhexyl)- adipates, sebacates, trimellitates and phthalates; epoxidised octyl stearate, epoxidised soya bean oil and phosphate esters of formula $O=P (OR^3)_3$ wherein $R^3$ is hydrocarbyl, particularly phenyl and especially $C_{1-4}$alkyl and low molecular weight oligo- and poly-esters such as those obtainable by reacting 1,3-butanediol with adipic acid.

According to a still further aspect of the invention there is provided a composition comprising a plasticiser and/or stabiliser for plastics materials together with component (a) and component (b).

According to another aspect of the invention there is provided a composition comprising a plastics material, component (a) and component (b).

As noted hereinbefore, the composition comprising component (a) and component (b) may be conveniently formulated with a carrier which is preferably a non-polar organic liquid, a polar organic liquid or water including mixtures thereof. The metal complex of the cyclic thiohydroxamic acid, which is component (b), is generally insoluble or only sparingly soluble in a carrier such as a non-polar organic liquid, polar organic liquid or water and consequently it is preferable to uniformly distribute the metal complex in the carrier by means of a dispersant. The isothiazolinones, which is component (a) of the composition, are mainly liquids and are generally soluble in organic liquids: This is especially true where component (a) is either N-n-octyl isothiazoline-3-one or 4,5-dichloro-N-n-octyl isothiazolin-3-one. Consequently, for many end-uses, the isothiazolinone may be dissolved in the organic liquid without recourse to the use of dispersants. However, when it is desirable to formulate such isothiazolinones in water as a carrier it is preferable to uniformly distribute the liquid isothiazolinone in the aqueous phase in the presence of an emulsifier. Where component (a) is a solid and the carrier is water, it is preferable to use a dispersant.

The choice of dispersant is dependent on the nature of the carrier. Thus, when the carrier is water, the dispersant is preferably anionic or non-ionic. Examples of suitable anionic dispersants are lignin sulphonates, polyacrylates, alkylaryl sulphonates and formaldehyde-naphthalene sulphonate condensates. Examples of suitable non-ionic dispersants are polyethers and especially the ethyleneoxide/propyleneoxide block copolymers, nonylphenolethoxylate, β-naphtholethoxylate, alcohol ethoxylates such as those obtainable from $C_{12-14}$-alcohols, amine ethoxylates and amide ethoxylates. When the carrier is a polar organic liquid, the dispersant is preferably a polyester, especially one obtainable by (co)polymerising a $C_{1-6}$-hydroxyalkylcarboxylic acid or lactone(s) thereof, and where the polyester is subsequently reacted with an amine or polyimine. Other preferred dispersants where the carrier is a polar organic liquid are polyester phosphates and polyisocyanates reacted with polyesters. When the carrier is a non-polar organic liquid, the dispersant is preferably a polyester derivable from a $C_{6-18}$-hydroxyalkylcarboxylic acid which is subsequently reacted with an amine or polyimine and optionally quaternised. Examples of suitable dispersants for non-polar organic liquids are the reaction product of 12-hydroxystearic acid and dimethylaminopropylamine which is quaternised with dimethylsulphate.

As noted hereinbefore, when component (a) is a liquid and the carrier is water it is preferable to formulate component (a) and component (b) in the presence of an emulsifier. Preferred emulsifiers are non-ionic and anionic and include alcohol ethoxy carboxylates, especially those obtainable from $C_{12-14}$-alcohols.

Dispersions containing solid component (b) and/or component (a) (if a solid) can be prepared by an means known to the art and include bead, pebble or ball milling the solid in the liquid carrier until the desired particle size of the solid is attained. Preferably, the particle size is less than 20, more preferably less than 10 and especially less than $5\mu$.

The dispersion may contain other adjuvants which stabilise solids in a liquid carrier. These include adjuvants which provide structure to the liquid carrier and inhibit separation and/or sedimentation of the solid. Where the carrier is an organic liquid, compounds which give structure to the organic liquid are polypropylene glycol, fused silica and naturally occurring clays such as bentonite and particularly organically treated clays. These organically treated clays are preferably used together with an activator such as mixtures of lower alcohol or propylene carbonate and water. The preferred ratio of propylene carbonate to water is 95:5. Where the liquid carrier is water, compounds which give structure to the water are: gums such as guar, xanthan, corrageenan and alginate; cellulosics such as carboxymethyl cellulose, hydroxyethyl cellulose and hydroxypropyl methyl cellulose; synthetic resins such as polyacrylamides, polyacrylates, polyvinylpyrolidone and polyvinyl alcohol. Xanthan gum is especially preferred.

When the composition contains a zinc salt of a thiohydroxamic acid additional zinc salts such as zinc acetate may also be added to enhance the long term stability of the thiohydroxamic acid.

The amount of dispersant in the dispersion depends on the type of solid and nature of the liquid carrier but is generally between 1 and 100% and preferably between 5 and 15% based on the amount of solid.

The amount of adjuvant which provides structure to the liquid carrier is preferably from 0.1 to 0.5% based on the total amount of the formulation.

Whereas the compositions of compounds of formula (2) and metal complexes of cyclic thiohydroxamic acids have been found to be particularly useful at inhibiting the. growth of deteriogens for plastics materials, they may also be used to protect other media, especially industrial media, which are susceptible to microbiological and especially fungal degradation. Examples of such industrial media are cooling tower liquors, metal working fluids, geological drilling muds, latices, paints, lacquers, wood, leather and pigments. Generally, the amount of the composition required to protect such industrial media is less than that required to protect plastics materials and good protection may be obtained with from 1 to 250 ppm and preferably from 1 to 100 ppm of the composition relative to the medium.

Thus, according to a further aspect of the invention there is provided a method for protecting a medium against microbiological degradation which comprises treating the medium with a composition comprising component (a) and component (b).

The invention is further illustrated by the following examples wherein all references to amount are in parts by weight unless expressed to the contrary.

EXAMPLE 1

Polyvinylchloride sheets were prepared by callendaring the following mixture at 160° C.

| 100 parts | Polyvinylchloride (Epivol SH65/20 ex. EVC) |
| 25 parts | Dioctylphthalate (ex. BP Chemicals) |
| 25 parts | Dioctyladipate (ex. BP Chemicals) |
| 2 parts | Mixed Ca/Zn salt stabiliser (Lankromark LN138 ex. Lankro Chem.) |
| 3 parts | Stabiliser/plasticiser (Lankroflex ED6 ex. Lankro Chem.) |
| 0.5 part | Calcium stearate (ex. Aldrich) |
| 0.2 part | Stearic acid (ex. Aldrich) |

Sheets were fabricated with the amount of biocide indicated in the following Table 1. Strips of the PVC sheets (8 parts, 12.5 x 5cm) were cut and weighed to 4 decimal places, folded and buried in potting compost (John Innes No.2) in a plastic humidity chamber. The compost was sprayed with a mixed inoculum of Aureobasidium pullulans, Fusarium solani, Penicillium funicularum, Scopulariopsis brevicaulis and Streptoverticillium waksmanii and incubated at 25° C. The PVC strips were examined at 4 week intervals when they were cleaned, dried and weighed. The weight loss after 20 weeks is recorded in Table 1 for the indicated combinations of Zinc Omadine/N-n-octyl isothiazolin-3-one (ZO/OIT) and Zinc Omadine/4,5-dichloro-N-n-octyl isothiazolin-3-one (ZO/DCOIT) which were all applied at 2000 ppm. The ratios of ZO/OIT and ZO/DCOIT are in parts by weight.

These data clearly show that the weight loss for the combinations of ZO/OIT and ZO/DCOIT is less than that expected from the data for the individual components.

TABLE 1

| Active | Amount | Actual % Weight Loss | Calculated % Weight Loss |
| --- | --- | --- | --- |
| ZO | 500 | 4.011 | — |
|  | 1000 | 3.557 | — |
|  | 2000 | 3.318 | — |
|  | 3000 | 2.179 | — |
| OIT | 1000 | 5.465 | — |
|  | 2000 | 3.47 | — |
|  | 3000 | 4.516 | — |
|  | 4000 | 4.992 | — |
| DCOIT | 500 | 7.398 | — |
|  | 1000 | 7.358 | — |
|  | 2000 | 7.818 | — |
|  | 3000 | 6.479 | — |
| ZO/OIT (1:3) | 2000 | 2.894 | 3.432 |
| ZO/OIT (1:1) | 2000 | 2.873 | 3.394 |
| ZO/OIT (3:1) | 2000 | 2.396 | 3.356 |
| ZO/DCOIT (1:3) | 2000 | 2.901 | 6.693 |
| ZO/DCOIT (1:1) | 2000 | 2.344 | 5.568 |
| ZO/DCOIT (3:1) | 2000 | 2.135 | 4.443 |
| CONTROL | — | 8.133 | — |

What is claimed is:
1. A method for the preservation of polyvinyl chloride or polyurethane which comprises treating the polyvinyl chloride or polyurethane with a composition comprising

(a) an isothiazolinone of formula 1

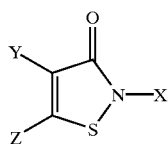
(1)

wherein
X is $C_{1-8}$alkyl, $C_{3-5}$-cycloalkyl or aralkyl; and
Y and Z are each, independently, hydrogen, halogen or $C_{1-4}$-alkyl; and
(b) a metal complex of a cyclic thiohydroxamic acid.

2. A method as claimed in claim 1 wherein component (a) is either N-n-octyl isothiazolin-3-one or 4,5-dichloro-N-n-octyl isothiazolin-3-one.

3. A method as claimed in either claim 1 or claim 2 wherein the cyclic thiohydroxamic acid is a compound of formula 2

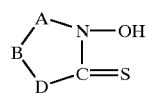
(2)

wherein
A is a group $—C(R^2)^2—$, $—C(R^2)=$ or $—CR^2=CR^2—$;
B is a group $—C(R^2)^2—$, $—C(R^2)=$ or $—C(NR^2)—$;
D is a group $—C(R^2)^2—$, $—C(R^2)=$, $NR^2—$ or sulphur; and
$R^2$ is hydrogen, optionally substituted $C_{1-6}$-hydrocarbyl or two groups $R^2$ together with the carbon atom to which they are attached form a $C_{3-6}$-hydrocarbon ring or two groups $R^2$ together with the two carbon atoms to which they are attached form a fused ring.

4. A method as claimed in claim 3 wherein A is the group $—CR^2=CR^2—$.

5. A method as claimed in claim 4 wherein $R^2$ is hydrogen.

6. A method as claimed in claim 1 wherein the metal is in zinc.

7. A method as claimed in claim 1 wherein component (b) is the 2:1 zinc complex of 1-hydroxypyridine-2-thione.

8. A method as claimed in claim 1 wherein the relative proportions of component (a) and component (b) is from 10:1 to 1:10.

9. A method according to claim 1, wherein X is said $C_{1-8}$-alkyl.

10. A method according to claim 1, wherein X is said $C_{3-5}$-cycloalkyl.

11. A method according to claim 1, wherein X is said aralkyl.

12. A composition comprising a plastics material comprising polyvinyl chloride or polyurethane and (a) N-n-octyl isothiazolin-3-one or 4,5-dichloro-N-n-octyl isothiazolin-3-one; and (b) a metal complex of a cyclic thiohydroxamic acid.

13. A composition according to claim 12, wherein (b) is either the 2:1 zinc complex of 3-hydroxy-4-methylthiazol-2(3H)thione or the 2:1 zinc complex of 1-hydroxypyridine-2-thione.

14. A composition according to claim 12, wherein the relative proportions of component (a) and component (b) is from 10:1 to 1:10.

15. A composition according to claim 12, further comprising a carrier.

16. A composition according to claim 15, wherein the carrier comprises a non-polar organic liquid, a polar organic liquid, water or mixtures thereof.

17. A composition according to claim 12, further comprising a dispersant, emulsifier or mixtures thereof.

18. A composition according to claim 12, further comprising a plasticizer, a stabilizer or mixtures thereof.

19. A master batch consisting essentially of:
(a) polyvinyl chloride or polyurethane;
(b) N-n-octyl isothiazolin-3-one or 4,5-dichloro-N-n-octyl isothiazolin-3-one; and
(c) a metal complex of a cyclic thiohydroxamic acid.

20. A method for preserving a plastics material, which comprises treating the plastics material with a composition comprising
(a) an isothiazolinone of formula 1

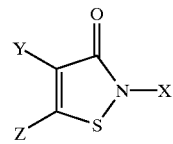
(1)

wherein
X is $C_{1-8}$-alkyl, $C_{3-5}$-cycloalkyl or aralkyl; and
Y and Z are each, independently, hydrogen, halogen or $C_{1-4}$-alkyl; and
(b) a metal complex of a cyclic thiohydroxamic acid;
wherein the plastics material is selected from polyvinylhalides, polyurethanes, polyalkylenes, polyalkylene vinyl acetates, polyesters and polyacrylonitriles.

21. A method according to claim 20, wherein (b) is the 2:1 zinc complex of 1-hydroxypyridine-2-thione.

22. A method according to claim 20, wherein (a) is N-n-octyl isothiazolin-3-one or 4,5-dichloro-N-n-octyl isothiazolin-3-one.

* * * * *